US012625132B2

(12) United States Patent
Bian et al.

(10) Patent No.: US 12,625,132 B2
(45) Date of Patent: May 12, 2026

(54) PORTABLE BLOWING TYPE ALCOHOL CONCENTRATION MEASURING DEVICE AND MEASURING METHOD

(71) Applicant: Jiangnan University, Wuxi City (CN)

(72) Inventors: Da Bian, Wuxi City (CN); Yi Chen, Wuxi City (CN); Yingji Li, Wuxi City (CN); Shanhua Qian, Wuxi City (CN); Zifeng Ni, Wuxi City (CN); Yongwu Zhao, Wuxi City (CN); Xiaohua Jia, Wuxi City (CN)

( * ) Notice: Subject to any disclaimer, the term of this patent is extended or adjusted under 35 U.S.C. 154(b) by 557 days.

(21) Appl. No.: 18/004,883

(22) PCT Filed: May 28, 2021

(86) PCT No.: PCT/CN2021/096566
§ 371 (c)(1),
(2) Date: Jan. 10, 2023

(87) PCT Pub. No.: WO2022/246775
PCT Pub. Date: Dec. 1, 2022

(65) Prior Publication Data
US 2023/0243808 A1     Aug. 3, 2023

(30) Foreign Application Priority Data

May 24, 2021    (CN) .......................... 202110566738.4

(51) Int. Cl.
*G01N 33/497* (2006.01)
*G01N 27/22* (2006.01)

(52) U.S. Cl.
CPC ....... *G01N 33/4972* (2013.01); *G01N 27/221* (2013.01); *G01N 27/226* (2013.01)

(58) Field of Classification Search
CPC ..... G01N 2035/00326; G01N 35/1065; G01N 35/00; G01N 35/0092; G01N 2035/00495;
(Continued)

(56) References Cited

U.S. PATENT DOCUMENTS 5,205,151 A * 4/1993 Shimamura .......... G01N 27/221
73/61.61
2003/0121309 A1* 7/2003 Fikus ................. G01N 27/4045
73/23.3
(Continued)

FOREIGN PATENT DOCUMENTS

CN     104487844 A     4/2015
CN     107153112 A  *  9/2017  ......... G01N 33/4972
(Continued)

OTHER PUBLICATIONS

Cai—CN109030399A_Included With English Translation—this reference is disclosed on IDS without translation (Year: 2018).*
(Continued)

*Primary Examiner* — Catherine T. Rastovski
*Assistant Examiner* — Toni D Sauncy

(57) ABSTRACT

A portable blowing alcohol concentration measuring device is provided, including: a housing, a valve body, a first one-way valve, a second one-way valve and a container. The first one-way valve can be opened and closed between the air inlet of the housing and the valve body; a container is provided at the other end of the housing, and the housing and the container are spaced by a PTFE membrane; the second one-way valve has a suction port connected to a drainage port on the container. The opening and closing of the second one-way valve can make the passage between the suction port and the inside of the valve body to achieve a pass-through. By optimizing the structure and testing method, the alcohol in the exhaled gas is fully dissolved in the solution
(Continued)

in the container, and the blood alcohol concentration can be
obtained by direct measurement using the fitted function.

6 Claims, 2 Drawing Sheets

(58) Field of Classification Search
CPC ....... G01N 33/4972; G01N 2015/1006; G01N
35/10; G01N 35/026; G01N 35/00871;
G01N 33/497; G01N 35/1072; G01N
33/92; G01N 35/04; G01N 2035/00306;
G01N 2035/0449; G01N 21/25; G01N
35/00069; G01N 33/5005; G01N
33/56983; G01N 15/1433; G01N
2035/00138; G01N 2035/00356; G01N
2035/00366; G01N 2035/00425; G01N
2035/0486; G01N 2035/0491; G01N
2201/024; G01N 2201/04; G01N
33/54366; G01N 33/98; G01N 35/00029;
G01N 35/1009; G01N 35/1011; G01N
2015/012; G01N 2015/016; G01N
2015/1486; G01N 2035/00148; G01N
2035/00237; G01N 2035/00435; G01N
2035/00633; G01N 2035/0474; G01N
2035/0493; G01N 2035/0494; G01N
21/27; G01N 2201/12; G01N 33/54306;
G01N 33/54313; G01N 33/56972; G01N
33/62; G01N 33/6827; G01N 33/80;
G01N 35/00623; G01N 2035/1051; G01N
1/40; G01N 21/76; G01N 1/24; G01N
2030/025; G01N 33/542; G01N
2001/2223; G01N 2015/0046; G01N
2035/00881; G01N 1/2202; G01N 33/50;
G01N 21/763; G01N 2333/726; G01N
2333/90241; G01N 33/5308; G01N
33/581; G01N 21/6428; G01N 21/783;
G01N 33/64; G01N 2021/0364; G01N
21/03; G01N 35/0099; G01N 2001/4027;
G01N 2015/0092; G01N 2030/328; G01N
2030/625; G01N 2030/626; G01N 21/31;
G01N 21/75; G01N 30/22; G01N
30/8606; G01N 30/8641; G01N 33/0006;
G01N 33/4975; G01N 33/53; G01N
33/948; G01N 2035/1076; G01N
21/3504; G01N 21/51; G01N 25/4873;
G01N 30/06; G01N 30/32; G01N
33/48707; G01N 33/5302; G01N 15/01;
G01N 2021/0321; G01N 2021/7786;
G01N 2035/00277; G01N 2035/0094;
G01N 33/52; G01N 2035/103; G01N
21/78; G01N 27/26; G01N 30/78; G01N
1/22; G01N 15/0205; G01N 15/06; G01N
2001/2244; G01N 21/0332; G01N 21/71;
G01N 21/8483; G01N 25/00; G01N
25/20; G01N 25/4813; G01N 2800/042;
G01N 2800/044; G01N 2800/347; G01N
2800/50; G01N 2800/52; G01N 31/22;
G01N 31/224; G01N 33/0008; G01N
33/6893; G01N 1/405; G01N 2001/028;
G01N 2021/6441; G01N 2030/324; G01N
2030/685; G01N 21/07; G01N 21/3518;
G01N 21/68; G01N 2405/04; G01N
2560/00; G01N 2800/325; G01N 33/582;
G01N 35/02; G01N 1/4077; G01N 15/14;
G01N 2001/4083; G01N 2021/3595;
G01N 2021/6439; G01N 2030/8827;
G01N 2035/1048; G01N 24/14; G01N
27/327; G01N 29/46; G01N 30/88; G01N
31/223; G01N 1/04; G01N 1/2273; G01N
2021/513; G01N 2021/6417; G01N
2035/1034; G01N 29/036; G01N 29/222;
G01N 30/02; G01N 33/0009; G01N
33/0011; G01N 33/0016; G01N 33/0019;
G01N 33/0021; G01N 33/0031; G01N
33/0036; G01N 33/22; G01N 33/225;
G01N 33/48; G01N 33/559; G01N
33/566; G01N 33/86; G01N 1/12; G01N
1/14; G01N 1/4022; G01N 2001/1418;
G01N 2001/2238; G01N 2001/2282;
G01N 2021/036; G01N 2021/825; G01N
2030/207; G01N 2035/00811; G01N
21/031; G01N 21/21; G01N 21/274;
G01N 21/35; G01N 21/3577; G01N
21/4133; G01N 21/62; G01N 21/645;
G01N 21/65; G01N 27/308; G01N
27/3335; G01N 27/416; G01N 30/08;
G01N 30/64; G01N 33/0054; G01N
33/007; G01N 33/18; G01N 33/182;
G01N 35/00732; G01N 35/0098; G01N
7/04; G01N 15/1434; G01N 15/1459;
G01N 2021/7769; G01N 2035/00158;
G01N 2035/00465; G01N 2035/00683;
G01N 2035/00772; G01N 2035/0403;
G01N 2035/0477; G01N 21/01; G01N
21/13; G01N 21/359; G01N 21/77; G01N
21/84; G01N 2201/021; G01N 2201/084;
G01N 2291/0255; G01N 2291/0256;
G01N 2291/0423; G01N 2333/11; G01N
2469/10; G01N 25/482; G01N 29/022;
G01N 29/2462; G01N 30/72; G01N
33/0072; G01N 33/14; G01N 33/487;
G01N 33/54373; G01N 33/5438; G01N
35/00584; G01N 1/2208; G01N 1/34;
G01N 1/44; G01N 15/0612; G01N
15/0656; G01N 2035/0429; G01N
2035/0441; G01N 21/66; G01N 21/67;
G01N 27/04; G01N 27/30; G01N
27/3272; G01N 27/4045; G01N 27/413;
G01N 27/4162; G01N 31/221; G01N
33/523; G01N 33/54386; G01N
33/56911; G01N 35/1095; B01L
2300/1827; B01L 7/52; B01L 9/06; B01L
3/5082; B01L 3/50855; B01L 3/5027;
B01L 2300/1855; B01L 3/021; B01L
9/52; B01L 9/543; B01L 2200/16; B01L
2300/0816; B01L 2200/0689; B01L
3/502715; B01L 2300/1822; B01L
2400/0409; B01L 2400/0487; B01L
2300/0636; B01L 2400/0677; B01L
3/0275; B01L 2300/0654; B01L 3/5021;
B01L 3/523; B01L 2300/0867; B01L
2300/0832; B01L 2200/141; B01L
2300/0681; B01L 2200/028; B01L
2300/0851; B01L 2200/0684; B01L
2300/069; B01L 3/0217; B01L 3/0279;
B01L 2200/0631; B01L 2200/0647; B01L
2200/082; B01L 2300/044; B01L
2300/0829; B01L 2300/0858; B01L
2300/1838; B01L 2400/043; B01L
3/5025; B01L 3/502738; B01L 3/502;

B01L 3/50825; B01L 2200/025; B01L
2300/0825; B01L 3/5023; B01L
2200/023; B01L 2200/0621; B01L
2200/0673; B01L 2300/041; B01L
2300/0883; B01L 2300/0893; B01L
2400/0644; B01L 2400/065; B01L
2400/0655; B01L 2400/0666; B01L
2400/0683; B01L 3/00; B01L 3/5029;
B01L 3/50851; B01L 9/527; B01L
2200/0605; B01L 2300/0663; B01L
2300/0896; B01L 2300/1805; B01L
2300/1877; B01L 2400/0622; B01L
2400/086; B01L 3/5085; B01L 3/52;
B01L 3/561; B01L 7/525; B01L 9/54;
B01L 2200/0663; B01L 2200/10; B01L
3/505; B01L 13/00; B01L 2200/027;
B01L 2200/0652; B01L 2300/045; B01L
2300/0627; B01L 2300/0645; B01L
2300/0887; B01L 2400/06; B01L
3/502761; B01L 2200/04; B01L
2300/0864; B01L 2400/0478; B01L
2400/049; B01L 2400/0605; B01L
2400/084; B01L 3/502784; B01L 9/523;
A61B 5/097; A61B 5/082; A61B
2018/00494; A61B 2018/0022; A61B
2018/0212; A61B 18/1492; A61B
2018/00577; A61B 2010/0087; A61B
2018/00791; A61B 10/0045; A61B 18/06;
A61B 10/00; A61B 5/087; A61B
5/14546; A61B 18/1815; A61B 18/24;
A61B 2018/00744; A61B 2018/00982;
A61B 2018/046; A61B 5/083; A61B
5/4845; A61B 10/0096; A61B 2010/0074;
A61B 2010/0216; A61B 18/02; A61B
2018/00011; A61B 2018/00255; A61B
2018/00285; A61B 2018/00291; A61B
2018/00642; A61B 2018/00839; A61B
2018/00863; A61B 2018/00875; A61B
5/01; A61B 5/14539; A61B 5/4839; A61B
5/6852; A61B 2560/0431; A61B
17/00234; A61B 17/00491; A61B
17/0218; A61B 17/3478; A61B 18/082;
A61B 2017/00004; A61B 2017/00022;
A61B 2017/00199; A61B 2017/00269;
A61B 2017/00818; A61B 2017/306;
A61B 2018/00005; A61B 2018/00017;
A61B 2018/00029; A61B 2018/00041;
A61B 2018/00559; A61B 2018/00672;
A61B 2018/00678; A61B 2018/00809;
A61B 2018/00815; A61B 2018/00821;
A61B 2018/1861; A61B 2090/3908;
A61B 2090/3933; A61B 2090/395; A61B
2218/002; A61B 2505/05; A61B
2560/0406; A61B 2562/227; A61B
5/0036; A61B 5/0066; A61B 5/0084;
A61B 5/055; A61B 5/42; A61B 5/4255;
A61B 5/4836; A61B 5/6885; A61B
2562/0276; A61B 2560/0443; A61B
5/073; A61B 10/0058; A61B 10/0291;
A61B 2010/008; A61B 2010/0208; A61B
2560/0214; A61B 5/0002; A61B 5/1486;
A61B 5/150358; A61B 5/150755; A61B
5/157; A61B 5/4362; A61B 5/7282; A61B
2562/0285; A61B 5/0836; A61B 5/14507;
A61B 5/18; A61B 5/74; A61B

2010/0006; A61B 2562/0233; A61B
5/036; A61B 5/0833; A61B 5/0878; A61B
5/091; A61B 5/14532; A61B 5/1455;
A61B 5/445; A61B 7/008; A61B
2090/064; A61B 5/0008; A61B 5/0803;
A61B 5/0823; A61B 5/0873; A61B
2018/00023; A61B 2560/0219; A61B
2560/0252; A61B 2560/0418; A61B
2562/0238; A61B 3/1241; A61B 3/16;
A61B 5/031; A61B 5/14555; A61B
5/416; A61B 5/4337; A61B 5/4872; A61B
5/6814; A61B 8/06; A61B 8/56; A61B
18/20; A61B 2560/0223; A61B 2562/08; A61B
2562/12; A61B 3/0025; A61B 3/0058;
A61B 3/10; A61B 3/14; A61B 3/185;
A61B 5/0031; A61B 5/053; A61B 5/062;
A61B 5/08; A61B 5/145; A61B 5/412;
A61B 5/6861; A61B 1/000094; A61B
1/00135; A61B 1/015; A61B 2017/00292;
A61B 2018/0016; A61B 2018/00648;
A61B 2018/00714; A61B 2090/061;
A61B 2560/0487; A61B 5/0059; A61B
5/201; A61B 5/413; A61B 2018/00214;
A61B 2018/00482; A61B 2018/044;
A61B 5/00; A61B 5/076; A61B 5/411;
A61B 5/7271; A61B 10/0064; A61B
18/14; A61B 2010/0003; A61B
2010/0009; A61B 2010/0061; A61B
2017/00106; A61B 2018/0025; A61B
2018/00261; A61B 2018/00273; A61B
2018/00761; A61B 2018/00773; A61B
2018/0237; A61B 2018/0262; A61B
2018/048; A61B 2503/22; A61B
2560/0242; A61B 2562/0247; A61B
2562/046; A61B 5/0022; A61B 5/0075;
A61B 5/14503; A61B 5/1451; A61B
5/14517; A61B 5/14552; A61B 5/1495;
A61B 5/150847; A61B 5/4244; A61B
5/4866; A61B 5/6833; A61B 5/6853;
A61B 5/688; A61B 5/6882; A61B
5/6893; A61B 5/7232; A61B 5/7275;
A61B 5/742; A61B 5/7475; A61B 8/483;
A61B 1/00016; A61B 1/00148; A61B
1/041; A61B 10/0051; A61B 10/04; A61B
17/3415; A61B 18/04; A61B 18/18; A61B
2018/00922; A61B 2505/09; A61B
2560/0257; A61B 2562/0295; A61B
2562/164; A61B 2562/168; A61B
2562/185; A61B 2576/00; A61B 5/0004;
A61B 5/02055; A61B 5/0816; A61B
5/093; A61B 5/1477; A61B 5/4238; A61B
5/6803; A61B 5/681; A61B 5/6821; A61B
5/6831; A61B 5/6832; A61B 5/6834;
A61B 5/6847; B01F 23/2133; B01F
23/21; B01F 23/20; B01F 23/213; B01F
23/405; B01F 25/43161; G01K 11/006;
G01K 11/22; G01K 13/20
See application file for complete search history.

(56) References Cited

U.S. PATENT DOCUMENTS

2014/0276100 A1* 9/2014 Satterfield ........... A61B 5/7271
600/476
2016/0242674 A1* 8/2016 Ahmad ................. A61B 5/082

(56)      References Cited

U.S. PATENT DOCUMENTS

| | | | | |
|---|---|---|---|---|
| 2017/0119279 A1 * | 5/2017 | Ahmad | .................. | A61B 10/00 |
| 2018/0074029 A1 | 3/2018 | Devries et al. | | |
| 2019/0344281 A1 * | 11/2019 | Ahmad | ................... | C12Q 1/25 |
| 2019/0350495 A1 * | 11/2019 | Ahmad | .................. | A61B 5/097 |

FOREIGN PATENT DOCUMENTS

| | | | |
|---|---|---|---|
| CN | 107290514 A | 10/2017 |
| CN | 207717772 U | 8/2018 |
| CN | 109030399 A | 12/2018 |
| CN | 111323607 A | 6/2020 |

OTHER PUBLICATIONS

Blaz, et al., "Capacitive Sensor for Quantity Detection of Known Liquid Present in Distilled Water", 37th Int. Spring Seminar on Electronics Technology, pp. 438-441 (Year: 2014).*

McCorkle, et. al., Ethanol vapor detection in aqueous environments using micro-capacitors and dielectric polymersâ, Sensors and Actuators B 107, 892-903 (Year: 2005).*

Selvam, et al., "A wearable biochemical sensor for monitoring alcohol consumption lifestyle through Ethyl glucuronide (EtG) detection in human sweat", Nature Scientific Reports 6, 23111 (Year: 2016).*

Liao—CN-107153112-A_Foreign patent doc-listed above— provided here With Translation (Year: 2016).*

International Search Report and Written Opinion of the corresponding PCT application No. PCT/CN2021/096566 mailed on Feb. 23, 2022.

* cited by examiner

PORTABLE BLOWING TYPE ALCOHOL CONCENTRATION MEASURING DEVICE AND MEASURING METHOD

FIELD OF THE INVENTION

The present invention relates to an alcohol concentration measuring device and its measuring method, specifically to a blowing type device for measuring the alcohol volume percentage in a mixed solution of alcohol and water and its measuring method.

BACKGROUND OF THE INVENTION

At present, it is difficult to directly measure the concentration of alcohol in a mixed solution of alcohol and water, and it is usually done by physical or chemical methods to separate the two, and then calculate and obtain the concentration of alcohol in them. The physical method is mainly based on the difference of boiling point of the two liquids to separate them by distillation, and then calculate the concentration of alcohol in them, while the chemical method is more difficult. These indirect measurement methods are not only time consuming, but also not very accurate and costly to test, and they cannot meet the requirements of use for measurements with high accuracy. Therefore, it has a very important meaning for finding a more efficient, more accurate and less cost method to test the alcohol volume percentage in blood. The conventional blood alcohol concentration measuring devices need to collect blood and are usually operated by hospital medical personnel, which are not suitable for general operators to operate portably, while other blowing type alcohol concentration measuring methods are subject to environmental and other factors that reduce the accuracy of measuring compared with blood measuring methods.

SUMMARY OF THE INVENTION

The purpose of the present invention is to provide a portable blowing type measuring device and measuring method for directly measuring the alcohol concentration in a mixed solution of alcohol and water or other liquids with good portability, low cost, and improved accuracy of blowing type alcohol measurement, so as to overcome the defects of the prior art.

The present invention uses the following technical solutions to achieve the above purpose.

In an embodiment, a portable blowing type alcohol concentration measuring device is provided, and the device comprises: a housing (4); a valve body (2) and a first one-way valve disposed inside the housing; a second one-way valve disposed on the housing; and a container (18), configured to hold a liquid, wherein one end of the housing has an air inlet, and the first one-way valve being openable and closeable is disposed between the air inlet and the valve body, the valve body inside has a cross-connected passage leading to the first one-way valve, the second one-way valve and the container, the container is disposed at another end of the housing, and the housing is separated from the container by a PTFE membrane (1), the container is provided with a drainage port (17) on a side wall near the end of the housing, the container is provided with an opening, and the opening being sealed by an openable and closeable sealing cap (16), the second one-way valve is disposed on a side wall of the housing, the second one-way valve has a suction port (14) connected with the drainage port on the container, and opening and closing of the second one-way valve realize connection and disconnection of the suction port and the passage inside the valve body.

In the embodiment, the first one-way valve comprises an inlet valve spring (6) and an inlet valve (7), wherein the inlet valve is movably disposed at an air inlet (15), and the inlet valve spring is disposed between the inlet valve and the valve body.

In the embodiment, the second one-way valve comprises a suction valve body (9), a suction valve steel ball (11) and a suction valve spring (13), wherein the suction valve body has a suction passage through the suction port and the valve body, the suction valve steel ball is movably disposed on the suction passage, so as to realize connection and disconnection between the suction port and the passage inside the valve body, and the suction valve spring is disposed between the suction valve steel ball and a side wall of the housing.

In the embodiment, the passage inside the valve body comprises a shaped flow passage (22) penetrating axially along the valve body and a transverse hole (23) crossed and penetrated with the shaped flow passage.

In the embodiment, the PTFE membrane allows the passage of gas and prevents the passage of liquid.

In the embodiment, the container is provided with a gas pressure sensor, a capacitance sensor and a temperature sensor, wherein the temperature sensor and the gas pressure sensor are connected to a signal processing unit, and the capacitance sensor is connected to the signal processing unit through an oscillation circuit, an amplification circuit, and an anti-interference circuit.

In a further embodiment, a measurement method based on the portable blowing type alcohol concentration measuring device is provided, and the method includes steps: step 1, blowing gas into the air inlet by tester, and the gas enters solution in the container through the first one-way valve and the valve body; step 2, collecting temperature t, capacitance C and gas pressure value P of the solution in the container; step 3, calculating a capacitance impact factor $\Delta C$ based on a temperature change $\Delta t$ at temperature t relative to a room temperature of 20° C. and a functional relationship equation (5) fitted by the capacitance impact factor $\Delta C$ and the temperature change $\Delta t$, $$\Delta C = b_0 + b_1 \Delta t + b_2 \Delta t^2 + b_3 \Delta t^3 \tag{5}$$

Where $b_0$, $b_1$, $b_2$, and $b_3$ are fitting coefficients for the function equation; using a functional relationship equation (3A) of modified capacitance C and the capacitance impact factor $\Delta C$ and alcohol volume percentage d in the solution to calculate the alcohol volume percentage d in the solution, $$C + \Delta C = a_0 + a_1 d' + a_2 d'^2 + a_3 d'^3 + \ldots a_k d'^k \tag{3A}$$

Where $a_0$, $a_1$, $a_2$, . . . $a_k$ are fitting coefficients and k is a set fitting polynomial order; using gas pressure value P measured by the gas pressure sensor to calculate actual volume $V_x$ of the blown-in gas via equation (6):

$$V_x = \frac{PV_1}{P_0} \tag{6}$$

Where $V_1$ is volume of the gas above the liquid in the container at temperature t, and $P_0$ is atmospheric pressure; using equation (7) to calculate alcohol volume percentage $d_0$ in the blown gas, $$d_0 = \frac{d'V_2}{V_x} \tag{7}$$

Where $V_2$ is volume of liquid in the container; using functional relationship equation (8) of alcohol volume percentage $d_0$ in the blown gas and alcohol volume percentage V in blood to calculate the alcohol volume percentage V in the blood, $$V = c_0 + c_1 d_0 + c_2 d_0^2 + c_3 d_0^3 \tag{8}$$

Where $c_0$, $c_1$, $c_2$, and $c_3$ are fitting coefficients.

In the further embodiment, the step of establishing a functional relationship equation of the capacitance C and the alcohol volume percentage d in the solution is:

A capacitance calculation equation according to equation (1):

$$C = \frac{2\pi\varepsilon_0\varepsilon_r L}{\ln(d_1/d_2)} \tag{1}$$

Where $\varepsilon_0$ is dielectric constant in vacuum, $\varepsilon_r$ is dielectric constant of mixed solution, L is orthogonal length of the two electrodes, $d_1$ is outer diameter of the capacitor, and $d_2$ is inner diameter of the capacitor; calculating the dielectric constant $\varepsilon_r$ of the mixed solution via the measured capacitance C when $\varepsilon_0$, L, $d_1$, and $d_2$ are given; calculating the alcohol volume percentage d in the solution by equation (2) according to the dielectric constant $\varepsilon_r$ of the mixed solution, a dielectric constant $\varepsilon_{r1}$ of pure alcohol, and a dielectric constant $\varepsilon_{r2}$ of pure water:

$$\sqrt{\varepsilon_r} = d\sqrt{\varepsilon_{r1}} + (1-d)\sqrt{\varepsilon_{r2}} \tag{2}$$

Establishing a relationship curve between the capacitance C and the alcohol volume percentage d in the solution based on the n actual measurements of the capacitance C and calculated corresponding alcohol volume percentages d in the solution, and fitting a function C=f(d) of relationship in-between the capacitance C and the alcohol volume percentage d according to equations (3) and (4) using the least squares method:

$$C = f(d) = a_0 + a_1 d + a_2 d^2 + a_3 d^3 + \dots \, a_k d^k \tag{3}$$

$$\text{Loss} = \sum_{i=1}^{n} \left[ C_i - \left( a_0 + a_1 d_i + a_2 d_i^2 + \dots \, a_k d_i^k \right) \right]^2 \tag{4}$$

Where Loss is an error sum of squares, the fitting objective of the least squares method is to minimize the error sum of squares, $C_i$ is a capacitance of the $i^{th}$ test, $d_i$ is a corresponding alcohol volume percentage calculated for the $i^{th}$ test, k≤n, and n is the total number of tests.

In the further embodiment, the method further includes: calibrating equation (3) using the capacitive impact factor $\Delta C$ to yield:

$$C + \Delta C = a_0 + a_1 d' + a_2 d'^2 + a_3 d'^3 + \dots \, a_k d'^k \tag{3A}.$$

In the further embodiment, steps of establishing a functional relationship equation of the alcohol volume percentage V in the blood and the alcohol volume percentage $d_0$ in the blown gas are: at the time when a tester finished blowing, measuring alcohol percentage in blood of the same tester; and fitting the functional relationship equation of the alcohol volume percentage V in the blood and the alcohol volume percentage $d_0$ in the blown gas according to measuring result of the blood of the tester.

Based on above, by optimizing the structure of the measuring device and the measuring method, the provided invention makes the alcohol in the blown gas dissolve in the liquid in the container as fully as possible, considers the impact of the different temperatures of different people blowing out the gas to the alcohol volume percentage in the blood, fits the relationship function by considering the impact of temperature, and uses of the fitted relationship function to achieve accurate results of the blood alcohol concentration, so as to avoid the way that collecting blood for measuring the blood alcohol concentration. Furthermore, the measuring device can be reused after replacing the liquid in the container, and has the advantages of simple operation, fast results, good portability, high testing efficiency and low testing cost.

BRIEF DESCRIPTION OF THE DRAWINGS

Embodiments of the invention are described in more details hereinafter with reference to the drawings, in which.

DETAILED DESCRIPTION

The present invention is further described below in conjunction with the accompanying drawings. The following embodiments are used only to illustrate the technical solutions of the present invention more clearly and cannot be used to limit the scope of protection of the present invention.

Embodiment 1

Figure 1:
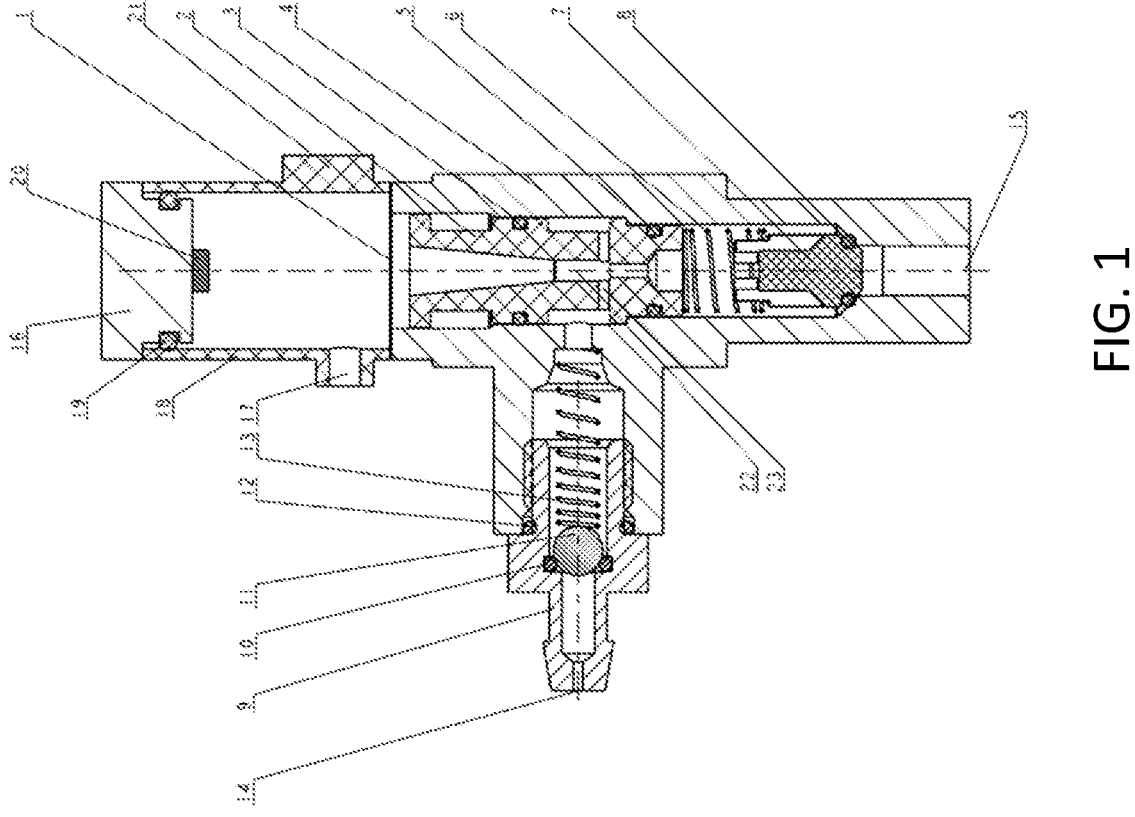
FIG. 1 depicts a cross-sectional view of a suction structure.

As shown in FIG. 1, the portable blowing type alcohol concentration measuring device of the embodiment includes a housing 4, a second one-way valve and container 18 disposed on the housing 4, a valve body 2 and a first one-way valve set inside the housing 4.

One an end of the housing 4 has an air inlet 15, the interior of the housing 4 is a hollow space, the internal hollow space is provided with a valve body 2 and the first one-way valve, and the first one-way valve is disposed close to the air inlet 15.

The valve body 2 is provided with a shaped flow passage 22 extending axially along the valve body 2, and the valve body 2 is also provided with a transverse hole 23 which extends radially along the valve body 2 and crosses through the shaped flow passage 22.

The function of the air inlet 15 is that it can be connected to a blowing tube, such that the gas blown by a tester can enter the valve body 2.

The first one-way valve mainly consists of an inlet valve spring 6 and an inlet valve 7. The inlet valve 7 is movably disposed at the air inlet 15, and the inlet valve spring 6 is disposed between the inlet valve 7 and the valve body 2. A seal ring 8 is also disposed between the inlet valve 7 and the air inlet 15, and a further seal is formed by the seal ring 8 between the inlet valve 7 and the air inlet 15 when the inlet valve 7 is held against the air inlet 15 by the elastic force of the inlet valve spring 6. The role of the first one-way valve is that, during the blowing stage, when the gas pressure entering from the air inlet 15 is higher than a sum of the preload force of the inlet valve spring 6 and the gas pressure inside the valve body 2, the inlet valve spring 6 is compressed, the first one-way valve is opened, and the gas may enter the valve body 2 through the first one-way valve; when entering the blowing completion stage, the gas pressure entering from the air inlet 15 is lower than the sum of the preload force of the inlet valve spring 6 and the gas pressure inside the valve body 2, the inlet valve spring 6 is uncompressed, the first one-way valve is closed, and the inlet valve 7 and the seal ring 8 at the air inlet 15 act as a seal, and the blown gas cannot enter from the air inlet 15 into the valve body 2, such that the gas inside the valve body 2 cannot be discharged from the air inlet 15.

Another end of the housing 4 is provided with a container 18, which is set adjacent to the valve body 2 inside the housing 4; the housing 4 and the container 18 are separated apart by a PTFE membrane 1. A side wall of one end of the container 18 near the housing 4 is provided with a drainage opening 17, and the function of the drainage opening 17 is let the liquid in the container 18 flow out from the drainage opening. The opening of the container 18 is sealed and blocked by a sealing cap 16. The container 18 is provided with a gas pressure sensor 20 for testing the gas pressure above the interior of the container 18. In this embodiment, the gas pressure sensor 20 is disposed on the surface of the sealing cap 16 facing the interior of the container 18, and in other embodiments, the location of the gas pressure sensor 20 can be specifically disposed as needed. A sealing ring 19 for sealing is disposed between the container 18 and the sealing cap 16. Item 21 is the mount for installing the capacitance sensor and the temperature sensor.

Figure 2:
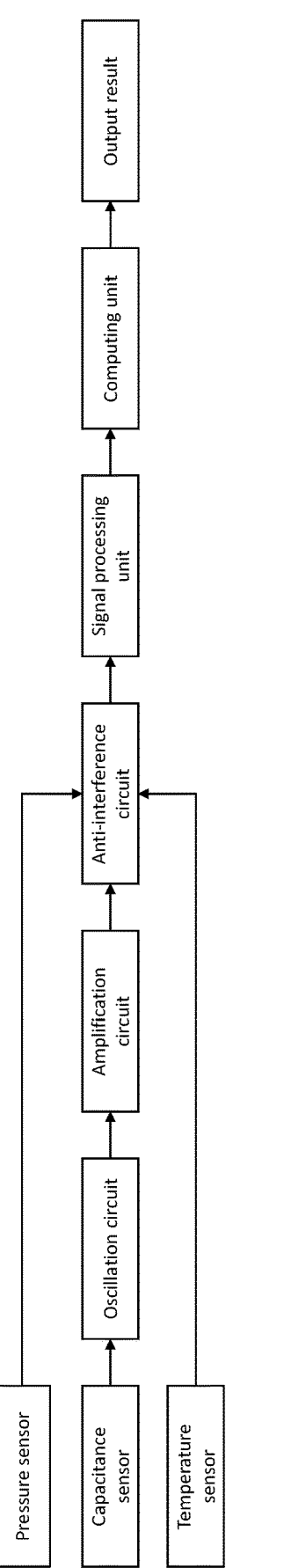
FIG. 2 depicts a workflow diagram of the measurement device for data acquisition.

As shown in FIG. 2, the container 18 is filled with a set amount of pure water, and the height of the pure water is submerged in the capacitance sensor and temperature sensor (not shown in the figure) disposed in the container 18 and lower than the gas pressure sensor 20, such that the gas pressure sensor 20 is exposed to the gas above the solution/liquid in the container 18. Both the temperature sensor and the gas pressure sensor 20 are connected to the signal processing unit, and the capacitance sensor is connected to the signal processing unit through an oscillation circuit, an amplification circuit, and an anti-interference circuit.

A second one-way valve is attached to a side wall of the housing 4 in a removable manner. The second one-way valve is mainly composed of a suction valve body 9, a suction valve steel ball 11 and a suction valve spring 13. Suction valve body 9 has a suction port 14, the suction port 14 is connected to the drainage port 17 on the container 18 through a pipe, and the water flowing out from the drainage port 17 can flow into the suction valve body 9 through the suction port 14, and at the same time, the suction port 14 can form a connection with the transverse hole 23 inside the valve body 2 through the suction valve body 9. The suction valve steel ball 11 can be movably disposed at the suction port 14, and the suction valve spring 13 is disposed between the suction valve steel ball 11 and the side wall of the housing 4.

A sealing ring 10 is disposed on a mating surface at which the suction valve body 9 may contact with the suction valve steel ball 11, when the suction valve steel ball 11 blocks on the suction port 14 of the suction valve body 9 because of the action of the suction valve spring 13, the suction valve steel ball 11 can be in contact with the seal ring 10 to seal the suction port 14. The preload force of the suction valve spring 13 is lower than the pressure difference generated by the water between the drain port 17 and the suction port 14. The function of the second one-way valve is that when the pressure of the suction port 14 is lower than the sum of the preload force of the suction valve spring 13 and the internal pressure of the valve body 2, the second one-way valve closes, and the suction valve steel ball 11 cooperates with the seal ring 10 to provide a sealing operation to prevent the gas inside the valve body 2 from flowing to the outside of the suction port 14; when the pressure of the suction port 14 is higher than the sum of the preload force of the suction valve spring 13 and the internal pressure of the valve body 2, the second one-way valve opens, then the water in the container 18 can enter inside the valve body 2 from the drainage port 17 through the suction port 14.

During the blowing stage, when the gas with higher flow speed blown into the inside of the valve body 2 passes through the shaped flow passage 22, the transverse hole 23 connected with the shaped flow passage 22 is in a negative pressure state, the second one-way valve opens, and the water at the suction port 14 can enter the transverse hole 23 due to gravitational potential energy.

PTFE membrane 1 is a layer of membrane that facilitates the passage of gas, but not the passage of liquid. The gas blown in from the air inlet 15 can enter into the container 18 through the PTFE membrane 1 and make full contact with the water inside the container 18, thus dissolving the blown-in gas fully in the water, while the solution inside the container 18 in reverse cannot directly penetrate into the valve body 2 and into the suction valve body 9 through the PTFE membrane 1.

Preferably, a sealing ring 12 seals between the suction valve body 9 and a side wall of the housing 4.

In this embodiment, for easy disassembly, the suction valve body 9 of the second one-way valve connects to the housing 4 in a threaded connection manner.

The function of the housing 4 is to support the valve body 2, the first one-way valve, container 18 and other parts, and provides the suction valve body 9 of the second one-way valve a threaded mounting interface, so as to implement a removable connection between the second one-way valve and the housing 4.

In order to increase the sealing between housing 4 and valve body 2, a sealing ring 3 and a sealing ring 5 can be disposed between housing 4 and valve body 2 for sealing.

Embodiment 2

The portable blowing type alcohol concentration measuring method of this embodiment, including following steps:
Step 1: Calibrate the Capacitive Sensor.

After connecting the capacitance sensor circuit, value displayed by the capacitance sensor is calibrated before conducting the test.

A table of dielectric constants at different alcohol volume percentage was calculated by equation (2), as shown in Table 1 below.

$$\sqrt{\varepsilon_r}=d\sqrt{\varepsilon_{r1}}+(1-d)\sqrt{\varepsilon_{r2}} \tag{2}$$

Where $\varepsilon_r$ is the dielectric constant of the mixed solution, i.e., the dielectric constant of the actual electrolyte; $\varepsilon_{r1}$ is the dielectric constant of pure alcohol; $\varepsilon_{r2}$ is the dielectric constant of pure water; and d is the alcohol volume percentage.

TABLE 1

| Dielectric constants at different alcohol volume percentages | | | | | | | | |
|---|---|---|---|---|---|---|---|---|
| Alcohol percentage | 0% | 1% | 2% | 3% | 4% | 5% | 6% | 100% |
| Dielectric constant of mixed solutions | 81 | 79.67 | 78.35 | 77.04 | 75.75 | 74.46 | 73.19 | 2.5 |

The capacitance sensor output value was calibrated according to the relationship between the calculated dielectric constant and the alcohol volume percentage in Table 1, and the test is started after the calibration is completed.

Step 2: Function Fitting.

Solutions with different alcohol concentrations (alcohol volume fraction) of T ° C. temperature are poured into the solution into the container 18 of the portable blowing type alcohol concentration measuring device respectively, such that each test is conducted by each solution having different alcohol concentrations. When measuring, the capacitance sensor is put in the solution, and the signal collected by the capacitance sensor is processed by the oscillation circuit, signal amplification circuit, and anti-interference circuit, and finally outputted to the signal processing unit, which calculates the outputted value of the alcohol volume percentage in the solution.

The capacitance calculation according to equation (1):

$$C = \frac{2\pi\varepsilon_0\varepsilon_r L}{\ln(d_1/d_2)} \qquad (1)$$

Where $\varepsilon_0$ is the dielectric constant in vacuum; $\varepsilon_r$ is the dielectric constant of the mixed solution, i.e., the dielectric constant of the actual electrolyte; L is the orthogonal length of two electrodes, $d_1$ is outer diameter of the capacitor; and $d_2$ is the inner diameter of the capacitor.

Calculating the dielectric constant $\varepsilon_r$ of the mixed solution via the measured capacitance C when $\varepsilon_0$, L, $d_1$, and $d_2$ are given.

Calculating the alcohol volume percentage d in the solution by equation (2) according to the dielectric constant $\varepsilon_r$ of the mixed solution, a dielectric constant $\varepsilon_{r1}$ of pure alcohol, and a dielectric constant $\varepsilon_{r2}$ of pure water:

$$\sqrt{\varepsilon_r} = d\sqrt{\varepsilon_{r1}} + (1-d)\sqrt{\varepsilon_{r2}} \qquad (2)$$

Establishing a relationship curve between the capacitance C and the alcohol volume percentage d in the solution based on the n actual measurements of the capacitance C and calculated corresponding alcohol volume percentages d in the solution, and fitting a function C=f(d) of relationship in-between the capacitance C and the alcohol volume percentage d according to equations (3) and (4) using the least squares method:

$$C = f(d) = a_0 + a_1 d + a_2 d^2 + a_3 d^3 + \dots a_k d^k \qquad (3)$$

$$\text{Loss} = \sum_{i=1}^{n} [C_i - (a_0 + a_1 d_i + a_2 d_i{}^2 + \dots a_k d_i{}^k)]^2 \qquad (4)$$

Where Loss is an error sum of squares, the fitting objective of the least squares method is to minimize the error sum of squares; $a_0$, $a_1$, $a_2$, . . . $a_k$ are fitting coefficients; k≤n, k is a set fitting polynomial order; $C_i$ is a capacitance of the $i^{th}$ test; $d_i$ is a corresponding alcohol volume percentage calculated for the $i^{th}$ test; and n is the total number of tests.

Considering that the temperature of human exhaled gas usually ranges from 10-40° C., changing the temperature of the solution in this range as $t_2$° C., $t_3$° C., $t_4$° C., etc., and repeating the above steps, so as to respectively obtain a function of the capacitance and the alcohol volume percentage at different temperatures via different tests. A capacitance value at room temperature of 20° C. is obtained, and yielding a fitted function of the capacitance impact factor $\Delta C$ with the change $\Delta t$ in temperature relative to the room temperature 20° C. as:

$$\Delta C = b_0 + b_1 \Delta t + b_2 \Delta t^2 + b_3 \Delta t^3 \qquad (5)$$

Where $b_0$, $b_1$, $b_2$, and $b_3$ are fitting coefficients for the function. Considering the calculation difficulty, calculation time and other factors, the order of the fitting polynomial related to the temperature is set to three orders in this embodiment.

Using the capacitance impact factor $\Delta C$ to calibrate fitting function equation (3) to yield equation (3A) as below:

$$C + \Delta C = a_0 + a_1 d' + a_2 d'^2 + a_3 d'^3 + \dots a_k d'^k \qquad (3A)$$

Step 3: Calibration a Function of Alcohol Volume Percentage in Blown Gas and Alcohol in Blood.

At the same temperature t, the volume of gas above the liquid in the container 18 is known as a fixed value $V_1$, the atmospheric pressure is $P_0$. For condition that different people blow a certain gas pressure, the actual volume of gas blown into the container is set to $V_x$, the gas pressure sensor 20 measured the gas pressure value P, and the actual volume of gas blown into the $V_x$ is:

$$V_x = \frac{PV_1}{P_0} \qquad (6)$$

The test using this device calculates different alcohol volume percentages d in the solution and the volume of pure water is $V_2$, then the alcohol volume percentage $d_0$ in the blown gas of the tester is:

$$d_0 = \frac{d'V_2}{V_x} \qquad (7)$$

To ensure a successive calibration, the alcohol volume percentage in the blood is measured to the tester at the time when the same tester has finished the blowing, and then a function for alcohol volume percentage V in the blood is fitted with the alcohol volume percentages do in the blown gas according to the blood test results:

$$V = c_0 + c_1 d_0 + c_2 d_0^2 + c_3 d_0^3 \qquad (8)$$

Where $c_0$, $c_1$, $c_2$, and $c_3$ are fitting coefficients.

This result (the fitting coefficients c0, c1, c2, and c3) is calibrated in the final displayed result function. Considering the calculation difficulty, calculation time and other factors, the order of the fitted polynomial in this embodiment is set to 3 orders.

Step 4: Measuring the Alcohol Volume Percentage in the Blood of the Tester.

Install the test device, connect the drainage port 17 and the suction port 14 with a pipe, connect the blowing tube on the air inlet 15, fill the container 18 with a fixed volume of pure water (the amount of pure water is set to let the surface of the pure water to be lower than the position of the gas pressure sensor 20), fix the gas pressure sensor 20 to the sealing cap 16, immerse the capacitance sensor and temperature sensor into the pure water of the container 18, connect to the test circuit of the sensors, fix the sealing cap 16 to the upper opening of the container 18; after connect the test system well, the tester blows the gas containing alcohol into the air inlet 15 through the blowing tube, the first one-way valve at the air inlet 15 opens under the action of airflow, the gas blown into the valve body 2 quickly into the shaped flow passage 22, and through the shaped flow passage 22 by penetrating the PTFE membrane 1 and then into the pure water in the container 18, part of alcohol gas is dissolved in the pure water. When the gas flows rapidly in the shaped flow passage 22 of the valve body 2, the pure water flows from the drainage port 17 to the suction port 14 under the action of gravitational potential energy difference, at this time, the second one-way valve at the suction port 14 opens under the action of gravitational potential energy of pure water and enters into the transverse hole 23 of the valve body 2 and into the shaped flow passage 22 crossed-through the transverse hole 23, and thus the alcohol gas in the blown gas is further dissolved into the pure water in this way, so as to achieve the purpose of full dissolution.

As each person's lung capacity is not the same, when the blowing reaches tester's blowing pressure limit, the blowing is stopped, and the first and second one-way valve at the air inlet 15 and suction port 14 are closed under the effect of the gas pressure in the container. As used herein, the term "tester" refers to a person (i.e., a human subject) who exhales gas into the device for measurement.

At this time, the capacitance sensor outputs the measured capacitance value through the oscillation circuit, amplification circuit, anti-interference circuit to the signal processing unit for signal processing; the gas pressure sensor 20 outputs the measured gas pressure value P, which is transmitted to the signal processing unit; the temperature sensor outputs the measured temperature value to the signal processing unit; performing corresponding calculation via a signal processing by the signal processing unit, and finally obtain the tester's alcohol volume percentage V in the blood.
The Calculation Process is:

Combined with the temperature measured by the temperature sensor to obtain the temperature change $\Delta t$ relative to the room temperature at 20° C.; according to the fitting functional equation (5), when $\Delta t$ is known, the capacitance impact factor $\Delta C$ can be calculated; on the basis of the capacitance C measured by the capacitance sensor, combining with the capacitance impact factor $\Delta C$, and using the fitting functional equation (3A), so as to obtain the alcohol volume percentage d in the solution; then using the gas pressure value P measured by the gas pressure sensor, using equations (6) and (7), so as to calculate the alcohol volume percentage $d_0$ in the blown gas; and finally calculating the alcohol volume percentage V in the blood of the tester according to the fitting functional equation (8).

It is important to note that the configuration and arrangement of the present application shown in a number of different exemplary embodiments are illustrative only. Although only a few embodiments are described in detail in this disclosure, it should be easy for those who refer to this disclosure to understand that many modifications are possible (for example, the size, scale, structure, shape and proportion of various elements, and parameter values (for example, temperature, pressure, etc.), installation arrangement, use of materials, color Changes in orientation, etc.). For example, an element shown as integrally formed may be composed of a plurality of parts or elements, the position of the elements may be inverted or otherwise changed, and the nature or number or position of discrete elements may be changed or changed. Therefore, all such modifications are intended to be included within the scope of the present invention. The order or sequence of any process or method steps may be changed or reordered according to alternative embodiments. In the claims, any "device plus function" clause is intended to cover the structure described herein for performing the function, and is not only structurally equivalent but also equivalent. Without departing from the scope of the invention, other substitutions, modifications, changes and omissions can be made in the design, operation status and layout of the exemplary embodiments. Therefore, the present invention is not limited to specific embodiments, but extends to a variety of modifications still falling within the scope of the appended claims.

In addition, in order to provide a concise description of exemplary embodiments, all features of the actual embodiments may not be described (that is, those features that are not related to the best mode of performing the invention currently considered, or those features that are not related to the implementation of the invention).

It should be understood that in the development process of any actual implementation, such as any engineering or design project, a large number of specific implementation decisions can be made. Such development efforts may be complex and time-consuming, but for those ordinary technicians who benefit from the public content, they do not need too much experimentation, and the development efforts will be a routine work of design, manufacturing and production.

It should be noted that the above embodiments are only used to illustrate the technical solution of the invention rather than limit it. Although the invention has been described in detail with reference to better embodiments, ordinary technicians in the art should understand that the technical solution of the invention can be modified or replaced equivalently without departing from the spirit and scope of the technical solution of the invention, which should be covered in the scope of claims of the invention.

What is claimed is:

1. A measurement method using a portable blowing type alcohol concentration measuring device, wherein the portable blowing type alcohol concentration measuring device comprises:

a housing (4);

a valve body (2) and a first one-way valve disposed inside the housing;

a second one-way valve disposed on the housing; and a container (18), configured to hold a liquid, wherein one end of the housing has an air inlet, and the first one-way valve being openable and closeable is disposed between the air inlet and the valve body, the valve body inside has a cross-connected passage leading to the first one-way valve, the second one-way valve and the container, the container is disposed at another end of the housing, and the housing is separated from the container by a PTFE membrane (1), the container is provided with a drainage port (17) on a side wall near the end of the housing, the container is provided with an opening, and the opening being sealed by an openable and closeable sealing cap (16), the second one-way valve is disposed on a side wall of the housing, the second one-way valve has a suction port (14) connected with the drainage port on the container, and opening and closing of the second one-way valve realize connection and disconnection of the suction port and the passage inside the valve body;

wherein the second one-way valve comprises a suction valve body (9), a suction valve steel ball (11) and a suction valve spring (13), wherein the suction valve body has a suction passage through the suction port and the valve body, the suction valve steel ball is movably disposed on the suction passage, so as to realize connection and disconnection between the suction port and the passage inside the valve body, and the suction valve spring is disposed between the suction valve steel ball and a side wall of the housing;

wherein the passage inside the valve body comprises a shaped flow passage (22) penetrating axially along the valve body and a transverse hole (23) crossed and penetrated with the shaped flow passage, such that during a blowing stage, gas flow through the shaped flow passage induces negative pressure at the transverse hole, resulting in opening of the second one-way valve and allowing water at the suction port to enter the transverse hole through the suction passage;

wherein the method comprises:

step 1, blowing gas into the air inlet by a human subject, wherein the gas enters solution in the container through the first one-way valve and the valve body;

step 2, collecting temperature t, capacitance C and gas pressure value P of the solution in the container;

step 3, calculating a capacitance impact factor $\Delta C$ based on a temperature change $\Delta t$ at temperature t relative to a room temperature of 20° C. and a functional relationship equation (5) fitted by the capacitance impact factor $\Delta C$ and the temperature change $\Delta t$, $$\Delta C = b_0 + b_1 \Delta t + b_2 \Delta t^2 + b_3 \Delta t^3 \tag{5}$$

where $b_0$, $b_1$, $b_2$, and $b_3$ are fitting coefficients for the function equation;

using a calibrated functional relationship equation (3A) of capacitance C and the capacitance impact factor $\Delta C$ and alcohol volume percentage d in the solution to calculate the alcohol volume percentage d in the solution, $$C + \Delta C = a_0 + a_1 d' + a_2 d'^2 + a_3 d'^3 + a_k d'^k \tag{3A}$$

where $a_0$, $a_1$, $a_2$, . . . $a_k$ are fitting coefficients and k is a set fitting polynomial order;

using gas pressure value P measured by the gas pressure sensor to calculate actual volume $V_x$ of the blown-in gas via equation (6):

$$V_x = \frac{PV_1}{P_0} \tag{6}$$

where $V_1$ is volume of the gas above the liquid in the container at temperature t, and $P_0$ is atmospheric pressure;

using equation (7) to calculate alcohol volume percentage $d_0$ in the blown gas, $$d_0 = \frac{d' V_2}{V_x} \tag{7}$$

where $V_2$ is volume of liquid in the container; and step 4, using functional relationship equation (8) of alcohol volume percentage $d_0$ in the blown gas and alcohol volume percentage V in blood to calculate the alcohol volume percentage V in the blood, $$V = c_0 + c_1 d_0 + c_2 d_0^2 + c_3 d_0^3 \tag{8}$$

where $c_0$, $c_1$, $c_2$, and $c_3$ are fitting coefficients.

2. The measurement method according to claim 1, wherein the step of establishing a functional relationship equation of the capacitance C and the alcohol volume percentage d in the solution is:

a capacitance calculation equation according to equation (1):

$$C = \frac{2\pi\varepsilon_0 \varepsilon_r L}{\ln(d_1/d_2)} \tag{1}$$

where $\varepsilon_0$ is dielectric constant in vacuum, $\varepsilon_r$ is dielectric constant of mixed solution, L is orthogonal length of the two electrodes, $d_1$ is outer diameter of the capacitor, and $d_2$ is inner diameter of the capacitor;

calculating the dielectric constant $\varepsilon_r$ of the mixed solution via the measured capacitance C when $\varepsilon_0$, L, $d_1$, and $d_2$ are given;

calculating the alcohol volume percentage d in the solution by equation (2) according to the dielectric constant $\varepsilon_r$ of the mixed solution, a dielectric constant $\varepsilon_{r1}$ of pure alcohol, and a dielectric constant $\varepsilon_{r2}$ of pure water:

$$\sqrt{\varepsilon_r} = d\sqrt{\varepsilon_{r1}} + (1-d)\sqrt{\varepsilon_{r2}} \tag{2}$$

establishing a relationship curve between the capacitance C and the alcohol volume percentage d in the solution based on the n actual measurements of the capacitance C and calculated corresponding alcohol volume percentages d in the solution, and fitting a function C=f(d) of relationship in-between the capacitance C and the alcohol volume percentage d according to equations (3) and (4) using the least squares method:

$$C = f(d) = a_0 + a_1 d + a_2 d^2 + a_3 d^3 + \dots a_k d^k \tag{3}$$

$$\text{Loss} = \sum_{i=1}^{n} \left[ C_i - \left( a_0 + a_1 d_i + a_2 d_i^2 + \dots a_k d_i^k \right) \right]^2 \tag{4}$$

where Loss is an error sum of squares, the fitting objective of the least squares method is to minimize the error sum of squares, $C_i$ is a capacitance of the $i^{th}$ test, $d_i$ is a corresponding alcohol volume percentage calculated for the $i^{th}$ test, k≤n, and n is the total number of tests.

3. The measurement method according to claim 2, further comprising:

calibrating equation (3) using the capacitive impact factor $\Delta C$ to yield:

$$C + \Delta C = a_0 + a_1 d' + a_2 d'^2 + a_3 d'^3 + \dots a_k d'^k \tag{3A}$$

4. The measurement method according to claim 1, wherein the first one-way valve comprises an inlet valve spring (6) and an inlet valve (7), wherein the inlet valve is movably disposed at an air inlet (15), and the inlet valve spring is disposed between the inlet valve and the valve body.

5. The measurement method according to claim 1, wherein the PTFE membrane allows the passage of gas and prevents the passage of liquid.

6. The measurement method according to claim 1, wherein the container is provided with a gas pressure sensor, a capacitance sensor and a temperature sensor, wherein the temperature sensor and the gas pressure sensor are connected to a signal processing unit, and the capacitance sensor is connected to the signal processing unit through an oscillation circuit, an amplification circuit, and an anti-interference circuit.

* * * * *